United States Patent [19]

Leifeld et al.

[11] Patent Number: 4,707,887
[45] Date of Patent: Nov. 24, 1987

[54] APPARATUS FOR DETECTING FOREIGN BODIES, SUCH AS PIECES OF METAL OR THE LIKE, IN TEXTILE FIBER BALES

[75] Inventors: Ferdinand Leifeld, Kempen; Paul Teichmann, Monchen-Gladbach, both of Fed. Rep. of Germany

[73] Assignee: Trützschler GmbH & Co. KG, Monchen-Gladbach, Fed. Rep. of Germany

[21] Appl. No.: 783,446

[22] Filed: Oct. 3, 1985

[30] Foreign Application Priority Data

Oct. 5, 1984 [DE] Fed. Rep. of Germany ....... 3436498

[51] Int. Cl.[4] .......................... D06H 3/14; D01G 9/00
[52] U.S. Cl. ........................................ 19/0.2; 19/80 R
[58] Field of Search ................ 19/0.2, 0.21, 0.22, 19/0.23, 80 R, 81, 239, 300; 26/70; 139/1 B, 348; 378/15, 146; 250/363 R, 363 S

[56] References Cited

U.S. PATENT DOCUMENTS

| | | | |
|---|---|---|---|
| 2,279,759 | 4/1942 | Moore | 139/1 B |
| 3,417,252 | 12/1968 | Nickell et al. | 26/70 X |
| 3,613,743 | 10/1971 | Sakamoto | 139/348 |
| 3,790,799 | 2/1974 | Stein | 378/146 |
| 3,971,103 | 7/1976 | Ono et al. | 19/0.2 |
| 4,167,803 | 9/1979 | Teichmann | 19/0.2 |
| 4,400,850 | 8/1983 | Burnett | 19/0.23 |

*Primary Examiner*—Louis K. Rimrodt
*Attorney, Agent, or Firm*—Spencer & Frank

[57] ABSTRACT

Apparatus for detecting a foreign body in a textile fiber bale. A search device is provided for detecting a foreign body in a textile fiber bale and a mechanism is provided for varying the location of the search device and of the fiber bale relative to one another.

18 Claims, 11 Drawing Figures

APPARATUS FOR DETECTING FOREIGN BODIES, SUCH AS PIECES OF METAL OR THE LIKE, IN TEXTILE FIBER BALES

BACKGROUND OF THE INVENTION

The present invention relates to an apparatus for determining the existence of a foreign body, such as a piece of metal or the like, in a textile fiber bale, the apparatus including a search device for detecting the foreign body.

The presence of a foreign body, such as a piece of iron banding, wire, a tool, etc., in a textile fiber bale may cause damage to the initial processing machine, for example, the bale opener, possibly starting a fire in that or a subsequent processing machine. Further, a foreign body in a fiber bale may undesirably get into further sections of the fiber processing system.

In a known device, mechanical sensor elements detect only electrically conductive foreign bodies. In order to be detected, however, these foreign bodies must be free of fiber tufts and must be disposed at the surface of the bale. The drawback of this device is that such exposed foreign bodies are not detected in time to prevent them from being removed, together with the uppermost layer of fiber tufts, by the initial processing machine and sucked into that machine. Further, it is generally already too late to avoid the removal and extraction of the foreign bodies, since a processing machine, such as a bale opener, cannot be shut off quickly enough to prevent such foreign bodies from entering the machine. Another annoying factor is that only foreign bodies having a size of a certain order of magnitude can be detected by the known detecting device. Smaller pieces such as bottle caps cannot be clearly identified.

SUMMARY OF THE INVENTION

It is therefore an object of the present invention to provide a device of the above-described type which avoids the above-mentioned drawbacks and which is also able to detect, in particular, a foreign body present in the interior of a fiber bale so that it can be removed, thus avoiding damage to the processing machinery.

The above and other objects are accomplishyed in accordance with the invention wherein an apparatus for detecting a foreign body in a textile fiber bale is provided which includes: a search means for detecting a foreign body in a textile fiber bale; and location means for varying the location of the search means and of the fiber bale relative to one another.

The foreign body search device according to one embodiment of the invention operates without contact with the fiber bale so that a foreign body present in the interior of the fiber bale can be detected in time before it comes into engagement with a processing machine. The foreign body thus can be removed before the fiber material is processed further. For example, the foreign body can be detected before it comes into contact with the processing members of the bale opener and thus before it may possibly damage them. At the same time, the foreign body can be removed from the fiber bale without removing fiber tufts and is prevented from entering a subsequent processing machine so that, for example, the sawtooth rolls of a subsequently connected cleaning device are protected against damage. The location of the foreign body search device and of the fiber bale relative to one another can be varied, thus moving the foreign body into the detection range of the foreign body search device.

One particular advantage of the invention is that it is able to operate with a small number of search devices which are moved relative to the bale or bales, respectively.

Advisably, the location of the foreign body search device can be varied with respect to stationary fiber bales. For example, the foreign body search device may be accommodated in a carriage next to which a separately arranged reserve bale group (that is a series of fiber bales placed freely one behind the other) are examined for foreign bodies. This determination is effected independently of the processing of the production bales, i.e. if a foreign body is detected, the production process is not interrupted.

It may also be of advantage to fasten the foreign body search device to the outrigger arm, the turret or the carriage of the bale opener if the bale opener is provided with at least one processing member, e.g. a fast running cutting device which is adjustable in height above the textile fiber bales. In this way, it is possible to examine the production bales during processing or the reserve bales which are arranged parallel to the production bales. Additionally, after a foreign body has been detected, an additional device provided in the processing member can remove the layer of fibers containing the foreign body and thus separate it from the fiber material not containing foreign bodies.

If relatively small foreign bodies are detected, which could cause malfunctions in the processing machine, the normal stream of material need not be interrupted but the portion of the material which contains the foreign body can be separated by way of a flap in the transporting device downstream of the machine. Preferably, the foreign body search device is disposed ahead of the processing device, e.g. the cutter, when seen in the direction of travel. In this way it is possible to detect and remove the foreign body before it comes in contact with the processing device.

According to another embodiment of the invention, the location of the fiber bales is variable with respect to the stationary foreign body search device, i.e. the bales can be moved or rolled. The production bales or the reserve bales are then moved past or below the stationary foreign body search device. For example, the reserve bales may be moved on a carriage or a roller conveyor in the direction toward the processing member. If the fiber bale is brought past a stationary foreign body search device equipped with a combination transmitter/receiver, the moving means must be associated with an electronic evaluation device and possibly a display screen. Preferably, the processing machine, e g. the bale opener, is braked and stopped when a foreign body is detected.

Advantageously the foreign body search device is able to process electromagnetic waves or radiation, such as X-rays, radar, ultrasound and the like. In this way it becomes possible to detect the foreign bodies within a bale without contacting them. Advisably, one selects such electromagnetic waves which have a penetration capability corresponding to length, width or height of a fiber bale. With such waves it is possible to operate either according to the transmitter/receiver principle or according to the echo principle which utilizes the beam reflected by the foreign body.

Preferably, an active foreign body search device is provided which is able to process waves or radiation capable of penetrating the fiber bales entirely or in part.

Advisably the foreign body search device includes a transmitter unit and a receiver unit. If a receiver chain composed of a plurality of receiving elements is assembled in such a length that it covers, for example, the entire height of a bale, one pass is sufficient to obtain an image of the foreign bodies contained in the fiber bale. A short receiver chain can be successively moved past the fiber bales together with the transmitter in different, successive planes or the fiber bale can be brought past the measuring device.

Advantageously, the transmitter unit is an X-ray transmitter including an X-ray generator and the receiver unit is an X-ray receiver including an X-ray detector. This embodiment has the advantage that it is possible to operate with a small number of foreign body search devices. For example, one X-ray generator (transmitter) may be sufficient. If very large areas are to be covered, the use of a plurality of such X-ray generators may be of advantage. If the bales are to be irradiated according to the X-ray principle, this may be done in that an X-ray source is brought past a bale surface and is oriented in such a way that its rays penetrate the fiber bale. A measuring cell or a series of measuring cells are arranged at the opposite side of the bale so as to be activated by the X-rays after they penetrate the bale. Advisably, the measuring cells are shielded against stray X-rays. The X-ray source and the measuring cells (sensors) have a fixed spatial relationship to one another. Commercially available X-ray units can be used as the radiation source. Scintillation crystals in conjunction with photodiodes can be used as the receiver unit.

It may also be of advantage to have a radar transmitter as the transmitter unit and a radar antenna as the receiver unit. According to the radar principle, a radar source and a radar receiver can be arranged next to one another so that a radar signal emanating from the radar transmitter impinges on a foreign body and is transmitted back to the receiver by reflection from the foreign body. By moving this transmitter and receiver unit with respect to the bales, the bales can be scanned at all spatial points. The movement may be a linear movement in the form of juxtaposed rows or a pivoting movement or a combination of both.

According to a further advantageous embodiment, a passive foreign body search device is provided. Advisably, the foreign body search device is an inductive coil. If the search coil has only a relatively small range (penetration depth), the search coil must be brought close to the surface of the fiber bale. To cover the whole area of the bale surface, a plurality of search coils are advisably provided. The search coils detect a foreign body below the bale surface within their effective range.

According to yet another embodiment, a capacitively acting device may be employed as the foreign body search device. Such a device influences a dielectric material disposed between the capacitor halves.

Advantageously an evaluation unit, e.g. a monitor, is connected to the receiver. In this way, it is possible to visually identify a foreign body with respect to its size, shape and position. For example, the surface of a bale can be scanned in successive lines by horizontally moving along a row of bales and making stepwise adjustments in the vertical direction. An electronic evaluation system with memory capability is associated with the scanning head. These memories may be oscilloscope screens, with points on the oscilloscope image corresponding to analog locations of scanning points on the surface of the bale. In the vicinity of the foreign body, the sensor member receives a signal which is displayed on the oscilloscope by differences in brightness or color. This makes it possible to display the size and position of a foreign body.

Advisably, a signalling unit is connected to the receiver to act, for example, optically or acoustically. In this way, it is possible to indicate the presence of a foreign body to a monitoring person who is not constantly present so that this person can turn off the machine.

The present invention will now be explained in greater detail with reference to embodiments that are illustrated in the drawings.

DESCRIPTION OF PREFERRED EMBODIMENTS

Figure 1A:
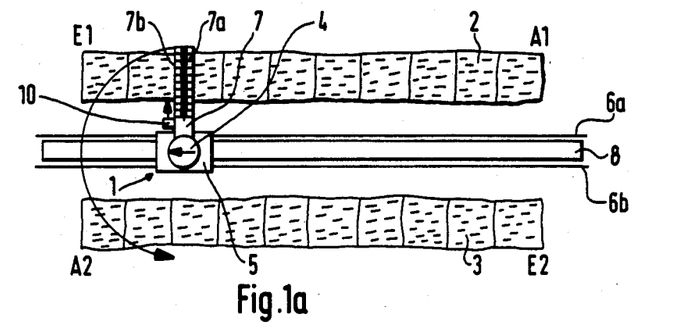
FIGS. 1a, 1b are schematics showing plan views of the apparatus according to two slightly different embodiments of the invention in which the apparatus is fasted to the carriage of a bale opener so as to be varied in location and move along a row of stationary fiber bales.
Figure 1B:
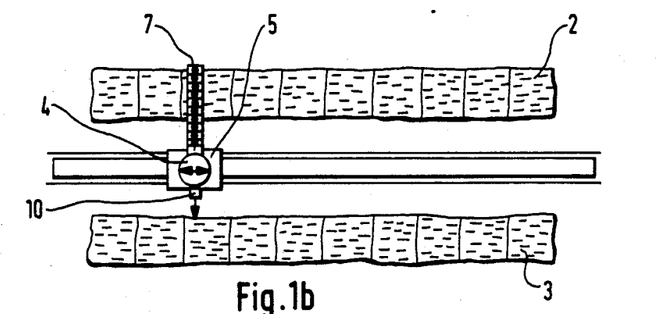

According to FIGS. 1a and 1b, a bale opener 1, for example, a BLENDOMAT made by Trützschler GmbH & Co., is comprised of a turret 4 for the removal of fiber tufts from fiber bales 2 and 3 which are arranged to form respective rows 2a and 3a. The turret is rotatably mounted on a movable carriage 5 and can be moved back and forth between the rows 2a and 3a by means of wheels which run on rails 6a and 6b. At its one side, turret 4 has an outrigger 7 and a detacher 7a which can be moved in the vertical direction (see FIG. 4). The detacher 7a, which may be, for example, a cutting device, removes fiber tufts from the surface of fiber bales 2 and 3. Below turret 4 and carriage 5, there is a channel 8 for receiving and transporting away the removed fiber tufts. In operation, carriage 5 and turret 4 move back and forth alongside, and the detacher 7a moves above, a respective one of the rows 2a and 3a of free-standing fiber bales 2 and 3, respectively. Starting at the beginning A1 of the row 2a of bales 2, carriage 5 moves towards end E1 (forward trip). At end E1, turret 4 and detacher 7 are rotated by 180° about a vertical axis, counterclockwise as shown in FIG 1a. This brings the detacher 7a to the start, A2, of the row 3a of bales 3. Beginning with start A2 of bale row 3a, carriage 5 travels to end E2 on the return trip.

According to the embodiment of FIG. 1a, in the region of one of its side faces 7b, upstream of detacher 7a, outrigger 7 is provided with a foreign body search device 10. Foreign body search device 10 may be active or passive and one or a plurality of foreign body search devices 10 may be provided. The arrow shows the direction of action of foreign body search device 10 in the direction toward bale row 2a. While bale rows 2a and 3a are being processed, foreign body search device 10 is adjusted downwardly in height and thus searches bale rows 2a and 3a row by row for foreign bodies.

According to the embodiment of FIG. 1b, bale row 2a (production bales) is processed first (see double arrow); bale row 3a (reserve bales) remains unchanged. Then turret 4 and outrigger 7 are rotated about 180° and bale row 3a is processed. At its side facing away from outrigger 7, turret 4 is provided with an adjustable height foreign body search device 10. While bale row 2a is being processed, that is while carriage 5 moves back and forth between bale rows 2a and 3a, foreign body search device 10 is adjusted downwardly in height and scans bale row 3a for foreign bodies.

Figure 1C:
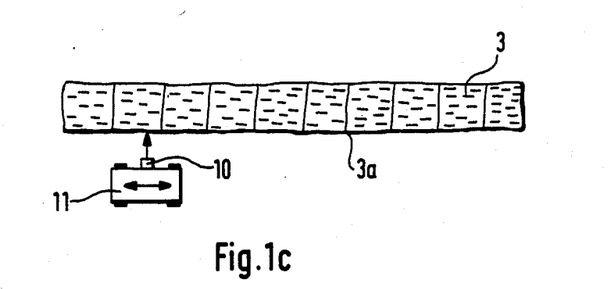
FIG. 1c is a schematic showing a plan view of another embodiment of the invention which includes the same apparatus according to the invention as in FIGS. 1a, 1b, but fastened to a separate carriage.

FIG. 1c shows an example of a bale row 3a (reserve bales) arranged in the bale storage area with a separate carriage 11 equipped with a foreign body search device 10 moving along its side. The arrow between foreign body search device 10 and side face 3b of row 3a indicates the direction of operation of foreign body search device 10.

Figure 2A:
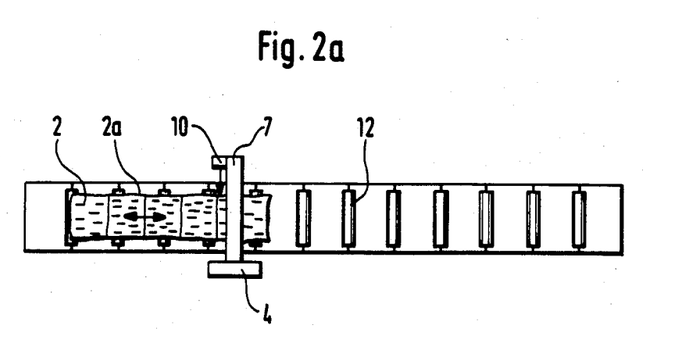
FIGS. 2a, 2b are schematics showing plan views of the apparatus according to another embodiment of the invention with a stationary foreign body search device past which the fiber bales are moved.

According to FIG. 2a, a stationary turret 4 is provided with a lateral, adjustable height outrigger 7. Bale row 2a moves back and forth on a roller conveyor 12 below cutting device 7a. On the side of outrigger 7, there is provided a foreign body search device 10 which, during processing, searches, i.e. irradiates, the interior of bale row 2a in the direction of its side face 2b to detect foreign bodies.

Figure 2B:
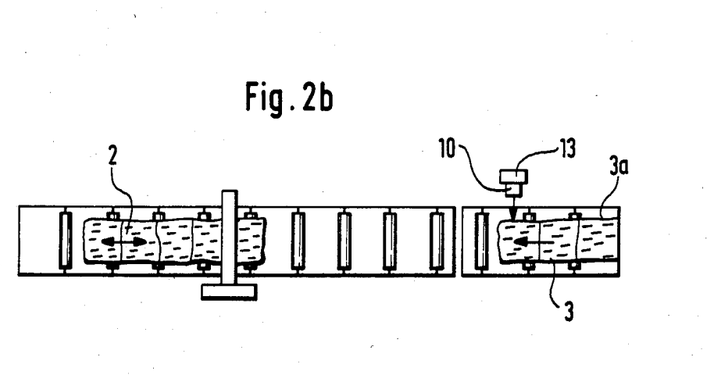

According to FIG. 2b, bale row 3a (reserve bales) is moved in the direction toward outrigger 7 as soon as bale row 2a (production bales) has been processed. During its movement (see arrow), bale row 3a passes by a stationary foreign body search device 10 which is disposed on the side of a holding element 13 in order to search the interior of bale row 3a for foreign bodies in the direction of its side face 3b.

Figure 3:
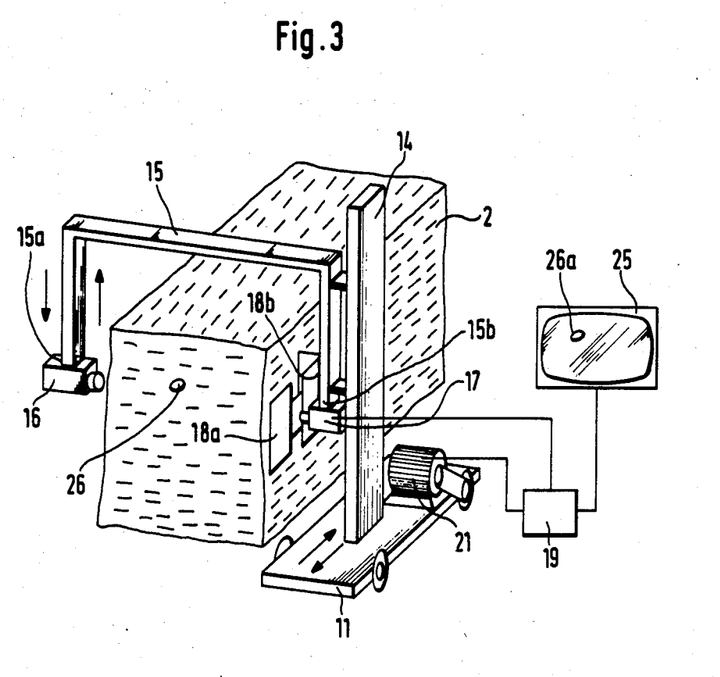
FIG. 3 is a schematic showing a perspective view of the apparatus according to a further embodiment of the invention in which a movable device is equipped with a transmitter and a receiver, with the receiver being connected with a drive and an optical evaluation unit including a monitor.

FIG. 3 shows a stationary bale row 2a, with a carriage 11 traveling back and forth along its side. Carriage 11 is equipped with a turret 14 having a U-shaped bar 15 with a downwardly oriented opening provided at its side in a height adjustable manner. At one end 15a of bar 15 there is fastened an X-ray transmitter 16. The other end 15b of bar 15 is provided with an X-ray receiver 17 and an aperture having two parts 18a, 18b. Receiver 17 is electrically connected with an electronic evaluation unit 19 which includes conventional measuring electronics, and which itself is connected, on the one hand, via a control device 20 (see FIG. 5) with a drive motor 21 for carriage 11 and, on the other hand, with a monitor 25. During operation, the X-rays radiate completely through the fiber bales 2 of bale row 2a, i.e. receiver 17 receives the radiation emanating from transmitter 16. Bale row 2a is penetrated by the radiation from the side, horizontally in the direction of travel, with bar 15 being adjusted vertically downwardly after each pass. In the region of a foreign body 26, for example a piece of metal, the radiation field is shielded so that a dark field is created on receiver 17 which appears on monitor 25 correspondingly as the image 26a of the foreign body.

Figure 4:
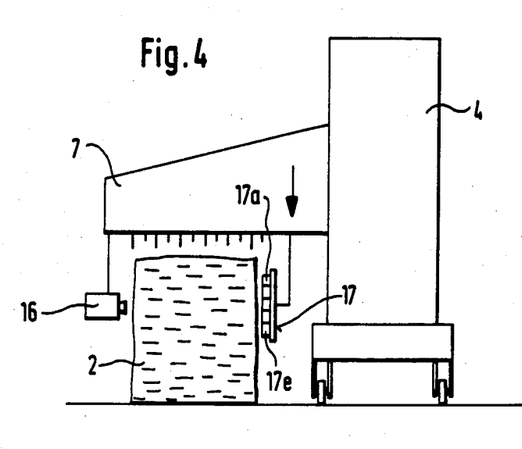
FIG. 4 is a schematic of a side view of the apparatus according to a further embodiment of the invention in which a movable device is attached to the adjustable height outrigger arm of a bale opener and includes a transmitter and a receiver chain.

According to FIG. 4, the receiver 17 and the aperture (not shown in FIG. 4) are disposed at the adjustable height outrigger 7 of turret 4 of a bale opener, e.g. a BLENDOMAT. Receiver 17 includes a plurality of receiving elements 17a to 17e and thus forms a receiver chain. In this way, a larger layer of the bale is irradiated in the vertical direction so that a smaller number of search passes are sufficient.

Figure 5:
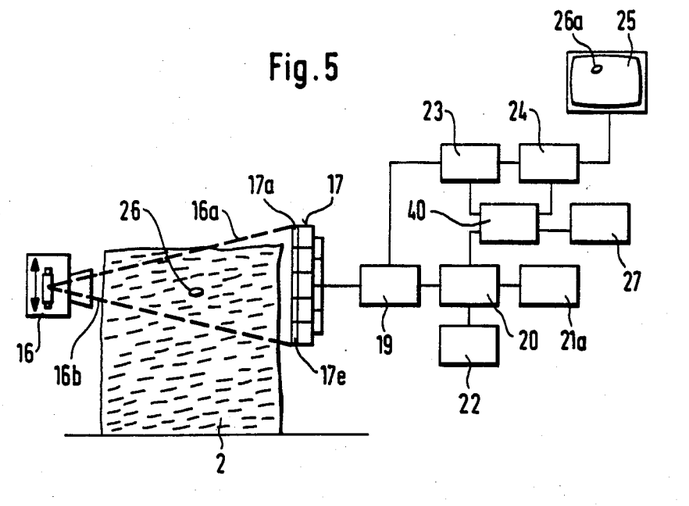
FIG. 5 is a schematic including a block circuit diagram of the devices of FIGS. 3 and 4.

According to FIG. 5, a commercially available X-ray transmitter 16 with X-ray generator emits X-ray radiation, the radiation field being illustrated by boundary lines 16a and 16b. After passing through bale 2, the X-rays impinge on X-ray receiver 17 composed of a linear row of detectors including units 17a to 17e, each equipped in a known manner with individual scintillation crystals. These crystals transfer their light to photodiode arrays, each composed of a plurality of silicon photodiodes. The integrated and amplified analog signals from the detector unit are digitalized in evaluation unit 19 and classified according to their gray stage characteristic. These signals travel to a subsequently connected image memory 23 where an image is composed and the image signal is passed on to monitor 25 via a digital to analog converter 24. A foreign body 26 in fiber bale 2 appears as image 26a. The signals coming from evaluation unit 19 are fed to an automatic control device 20 which generates a signal to switch off the drive motors (e.g. motor 21 and drive motor 21a for processing member 7a) of bale opener 1 and for an optical display device, e.g. a lamp 22. The signals from control device 20 can also be fed to a computer 26; or computer 26 may receive signals for further processing, for example to automatically remove foreign body 26 by way of a removal device 27, or for evaluation or the like, and may be connected to monitor 25 via digital to analog converter 24.

Figure 6:
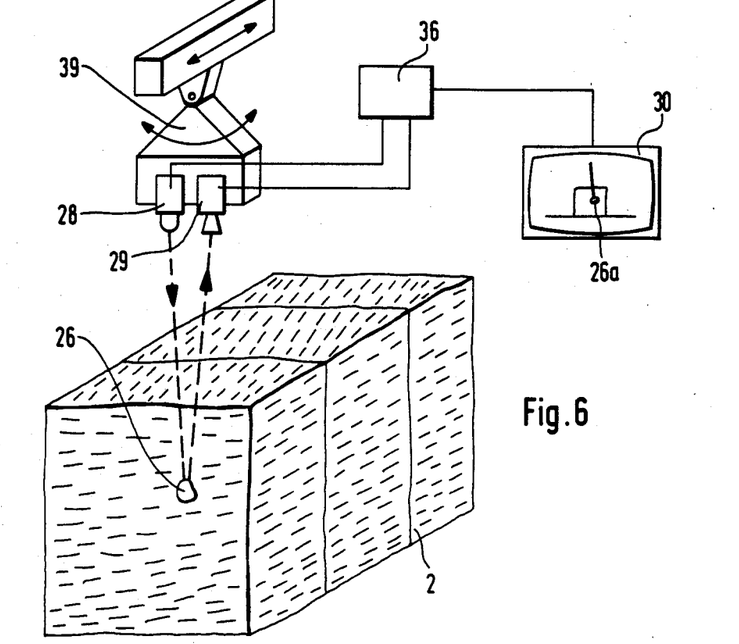
FIG. 6 is a perspective view the apparatus according to another embodiment of the invention wherein a movable device includes a radar transmitter and a radar receiver.

FIG. 6 shows a stationary bale row 2a, above which a pivotal holding element 31 is provided at a movable holding device (not shown) with a radar transmitter 28 (transmitting antenna) and a radar receiver 29 (receiving antenna) being fastened thereto. Radar transmitter 28 and radar receiver 29 are connected with an electronic evaluation unit 36 to which is connected an evaluation monitor 30. The transmitting antenna of radar transmitter 29 transmits a sharply bundled signal (short, high frequency pulse of about 2 μs). If this signal impinges on a foreign body 26 in a fiber bale 2, a return pulse (echo) is initiated which returns to radar receiver 29 (echo). The foreign body 26 marked by the echo is made visible on the screen of monitor 30 as shown at 26a. The radar system operates, for example, in the microwave range.

Figure 7:
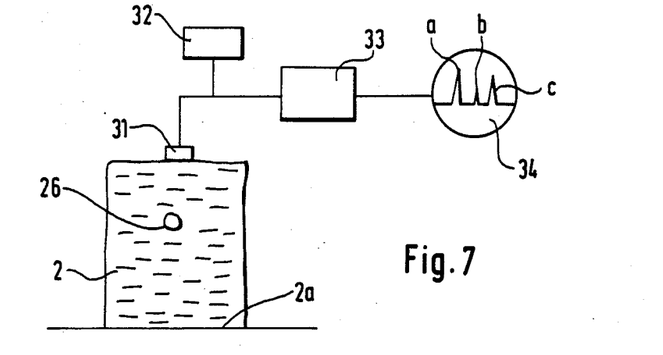
FIG. 7 is a schematic including a block circuit diagram of a device comprising a sound generator and a sound receiver according to another embodiment of the invention.

FIG. 7 shows a hard pressed fiber bale 2 onto which a sound generator, including, for example a quartz crystal, for generating ultrasonic waves, has been placed. Short sound surges (pulses) are transmitted into fiber bale 2. Pulse generator 32 acts on transmitting quartz crystal 31 as well as on receiving amplifier 33. The pulse given to transmitting quartz crystal 31 becomes visible on the screen 34 of a cathode-ray oscillograph. On the other hand, during periods of inactivity, transmitting quartz crystal 31 can operate as a sound receiver in the rest periods between pulses. The pulse switched into fiber bale 2 partially impinges on a foreign body 26 and partially on the opposite wall 2b, is reflected by both and received again by quartz crystal 31. Transmitted pulse a, echo b from foreign body 26 and counterwall echo c from wall 2b are shown on screen 34.

Figure 8:
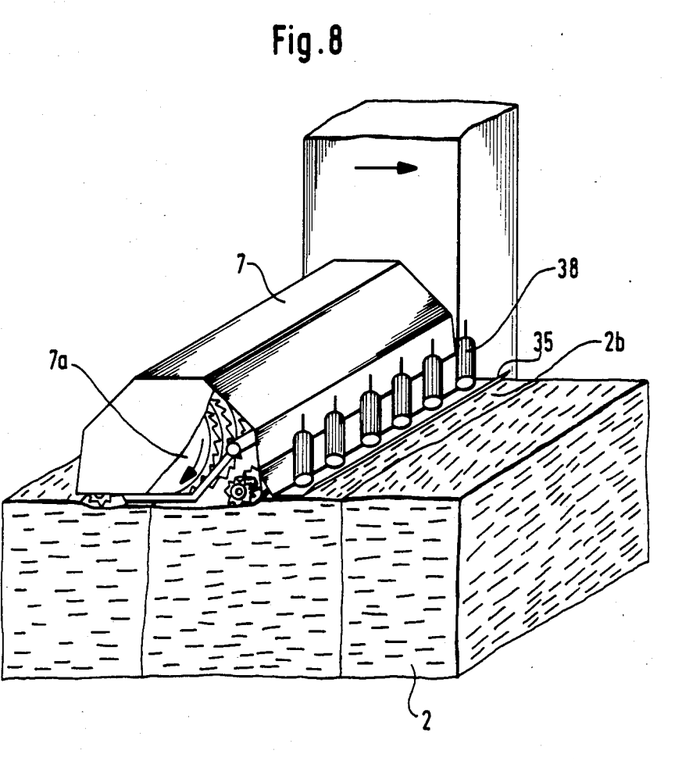
FIG. 8 is a schematic showing a perspective view of another embodiment of the invention including a device having a plurality of inductive foreign body search devices in the form of search coils.

According to FIG. 8, outrigger 7 of a bale opener, e.g. a BLENDOMAT and detacher 7a are provided above fiber bales 2. An inductive slide rod 35 is fastened to the side of outrigger 7 and is provided with a plurality of inductive switches 36, e.g. BERO switches which are inductive proximity switches maufactured by Siemens AG, Munich, Federal Republic of Germany. Slide rod 35 slides resiliently on surface 2c of the fiber bales, that is it exerts contact pressure onto surface 2c. This brings switches 36 as close as possible to foreign body 26 so that foreign body 26 comes into the effective range 36a (See FIG. 8a) of switches 36. In this way it is possible to detect foreign bodies 26 which are disposed relatively closely below surface 2c, but outside the engagement range of processing member 7a.

Figure 8A:
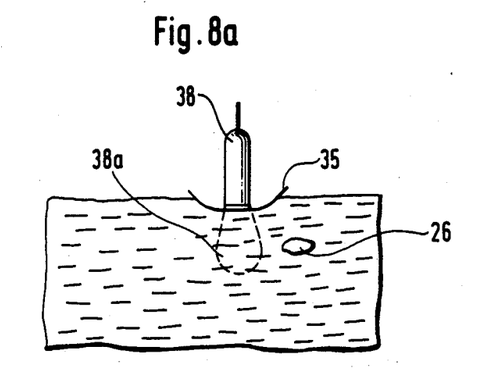
FIG. 8a is a detail view of the inductive search coil shown in FIG. 8 with respect to the fiber bale and a foreign body.

FIG. 8a is a detail view of inductive switch 36 on bent-open slide rod 35. Slide rod 35 may be interrupted in the manner of a grate, with the grid bars sliding on surface 2c and switch 36 being disposed above the gaps of the grate.

Figure 9:
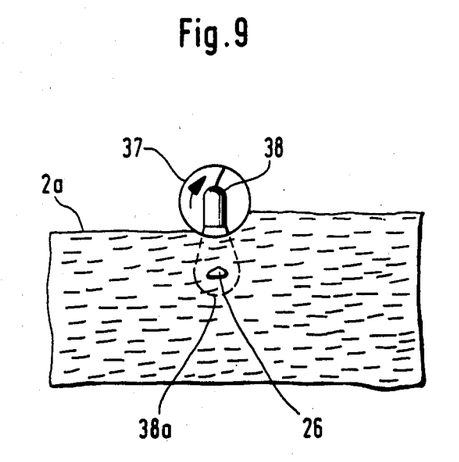
FIG. 9 is a schematic showing a device including a contact roll according to yet a further embodiment of the invention.

FIG. 9 shows a roller 37, for example provided with a plastic coating, rolling on surface 2c in contact with the fiber bales. In the interior of roller 37 there are provided a plurality of inductive switches 36 or, alternatively, capacitive measuring elements. Roller 37 produces rolling friction and is attached, for example, upstream of outrigger 7 (see FIG. 8) of a bale opener 1. The foreign body is marked with the numeral 26. The effective range of switch 36 is marked 36a.

The invention may be implemented with a foreign body search device with an X-ray apparatus such as that disclosed by H. Schaffrath in the periodical *Kunststoffe* [*Plastics*], No. 4, April 1953, pages 138 to 140. The X-ray apparatus there disclosed is used for the determination of small metal particles in the field of plastics processing. The X-ray examination of metal particles in the interior of a compressed fiber bale in accordance with the present invention is not therein disclosed. Further, evaluation units for the evaluation of X-rays are commercially available and known per se. German Offenlegungsschrift [German Laid-Open Patent Application] No. 2,312,204 describes a device for ultrasonic testing which includes an evaluation unit. Again, the use of such an ultrasonic testing device in connection with fiber bales pursuant to the present invention is not disclosed in the above noted German Offenlegungsschrift. Additionally, an inductive coil which may be used to implement the foreign body search device according to the present invention is disclosed in U.S. Pat. No. 4,171,262 which discloses an inductive coil device for separating metallic foreign bodies from a fiber transporting conduit (as opposed to the interior of a compressed fiber bale as in the present invention).

It will be understood that the above description of the present invention is susceptible to various modifications, changes and adaptations, and the same are intended to be comprehended within the meaning and range of equivalents of the appended claims.

What is claimed is:

1. In a bale opener arranged for a back-and-forth travel along a series of stationarily supported fiber bales, including a detaching means supported above the fiber bales for progressively removing fiber tufts from upper bale faces during travel ofthe bale opener; the improvement comprising search means for detecting foreign bodies in the fiber bales during operation of the bale opener; said search means being mounted on said bale opener for travel therewith; said search means being situated upstream of the detaching means as viewed in the direction of movement of said bale opener and being oriented to scan the stationary fiber bale being worked on by the bale opener for detecting foreign bodies at locations within the fiber bale prior to an arrival of said detaching means in said locations.

2. A bale opener as defined in claim 1, further comprising a motor for driving said detaching means; and braking means for stopping the motor; said search means being connected to said braking means for stopping operation of said detaching means upon detecting a foreign body by said search means.

3. Apparatus as defined in claim 1, wherein said search means includes means for processing electromagnetic radiation.

4. Apparatus as defined in claim 1, wherein said search means is an active device and includes means for processing radiation which can completely or partially penetrate a fiber bale.

5. Apparatus as defined in claim 1, wherein said search means includes a transmitting unit and a receiving unit.

6. Apparatus as defined in claim 5, wherein said transmitting unit is an X-ray transmitter and said receiving unit is an X-ray receiver.

7. Apparatus as defined in claim 5, wherein said transmitting unit is a radar transmitter and said receiving unit is a radar antenna.

8. Apparatus as defined in claim 5, wherein said transmitting unit is a sound generator and said receiving unit is a sound receiver.

9. Apparatus as defined in claim 5, including an evaluation means connected to said receiver unit for evaluating signals produced by said receiver unit.

10. Apparatus as defined in claim 9, including a monitor connected to said evaluation unit.

11. Apparatus as defined in claim 1, wherein said search means is a passive device.

12. Apparatus as defined in claim 11, wherein said search means is an inductive coil.

13. Apparatus as defined in claim 11, wherein said search means comprises capacitive elements.

14. Apparatus as defined of claim 1 including signalling means coupled for receiving an output signal from said search means and for producing a signal indicating the presence of a foreign body in response to the output signal from said search means.

15. Apparatus as defined in claim 14, wherein said signalling means produces an optical signal.

16. Apparatus as defined in claim 1, wherein said search means comprises a plurality of search devices and mounting means for mounting said plurality of search devices, said mounting means being arranged for contacting the surface of a fiber bale.

17. Apparatus as defined in claim 16, wherein said mounting means comprises a slide rod which is arranged for making sliding contact with the surface of a fiber bale.

18. Apparatus as defined in claim 17, wherein said mounting means comprises a contact roller which is arranged for making rolling contact with the surface of a fiber bale.

* * * * *

UNITED STATES PATENT AND TRADEMARK OFFICE
CERTIFICATE OF CORRECTION

PATENT NO. : 4,707,887

DATED : November 24, 1987

INVENTOR(S) : Ferdinand Leifeld et al.

It is certified that error appears in the above-identified patent and that said Letters Patent is hereby corrected as shown below:

In the drawing, Fig. 1a, Fig. 1b, Fig. 1c, Fig. 2a, Fig. 2b, Fig. 3, Fig. 4, Fig. 5, Fig. 6, Fig. 7 and Fig. 8, should appear as shown on the attached sheets.

Signed and Sealed this

Twelfth Day of April, 1988

*Attest:*

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,707,887                                 Page 2 of 7

DATED      : November 24th, 1987

INVENTOR(S): Ferdinand Leifeld et al

It is certified that error appears in the drawings of the above-identified patent and that said Letters Patent is hereby corrected as shown below:

UNITED STATES PATENT AND TRADEMARK OFFICE
CERTIFICATE OF CORRECTION

PATENT NO. : 4,707,887

DATED : November 24th, 1987

INVENTOR(S) : Ferdinand Leifeld et al

Page 3 of 7

It is certified that error appears in the drawings of the above-identified patent and that said Letters Patent is hereby corrected as shown below:

Fig. 2a

Fig. 2b

UNITED STATES PATENT AND TRADEMARK OFFICE
CERTIFICATE OF CORRECTION

PATENT NO. : 4,707,887  Page 4 of 7

DATED : November 24th, 1987

INVENTOR(S) : Ferdinand Leifeld et al

It is certified that error appears in the drawings of the above-identified patent and that said Letters Patent is hereby corrected as shown below:

Fig.3

UNITED STATES PATENT AND TRADEMARK OFFICE
CERTIFICATE OF CORRECTION

PATENT NO. : 4,707,887

DATED : November 24th, 1987

INVENTOR(S) : Ferdinand Leifeld et al

Page 5 of 7

It is certified that error appears in the drawings of the above-identified patent and that said Letters Patent is hereby corrected as shown below:

UNITED STATES PATENT AND TRADEMARK OFFICE
CERTIFICATE OF CORRECTION

PATENT NO. : 4,707,887

DATED : November 24th, 1987

INVENTOR(S) : Ferdinand Leifeld et al

It is certified that error appears in the drawings of the above-identified patent and that said Letters Patent is hereby corrected as shown below:

Fig.6

Fig.7

UNITED STATES PATENT AND TRADEMARK OFFICE
CERTIFICATE OF CORRECTION

PATENT NO. : 4,707,887

DATED : November 24th, 1987

INVENTOR(S) : Ferdinand Leifeld et al

It is certified that error appears in the drawings of the above-identified patent and that said Letters Patent is hereby corrected as shown below:

Fig.8